(12) United States Patent
Wu-Wong et al.

(10) Patent No.: US 6,284,882 B1
(45) Date of Patent: Sep. 4, 2001

(54) MYOSTATIN GENE PROMOTER AND INHIBITION OF ACTIVATION THEREOF

(75) Inventors: Jinshyun R. Wu-Wong, Lake Bluff; Jiahong Wang, Northbrook, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/329,685

(22) Filed: Jun. 10, 1999

(51) Int. Cl.[7] .............................. C12N 5/00; C12N 15/00; C07H 21/04
(52) U.S. Cl. ...................... 536/24.1; 435/325; 435/320.1
(58) Field of Search ..................... 536/24.1; 435/325, 435/320.1

(56) References Cited

FOREIGN PATENT DOCUMENTS 1 072 680 A1    1/2001   (EP) .

OTHER PUBLICATIONS

A. C. McPherron et al., Regulation of Skeletal Muscle Mass in Mice by a New TGF–β Superfamily Member, Nature vol. 387 / May 1, 1997 pp. 83–90.

N. F. Gonzalez–Cadavid et al., "Organization of the Human Myostatin Gene and Expression in Healthy Men and HIV–Infected Men With Muscle Wasting", Proc. Natl. Acad. Sci. USA—vol. 95, pp. 14938–14943, Dec. 1998—Medical Sciences.

H. Wada et al., "T Cell Functions In Granulocyte/Macrophage Colony–Stimulating Factor Deficient Mice", Proc. Natl. Acad. Sci. USA, vol. 94, pp. 12557–12561, Nov. 1997—Immunology.

Wang, et al., *Journal of Immunological Methods*, Determination of Heparin–Induced IgG Antibody by Fluorescence–Linked Immunofiltration Assay (FLIFA), 222:93–99 (1999).

Ausubel, et al., *Current Protocols in Molecular Biology*, Enzyme–Linked Immunosorbent Assays (ELISA), United States of America XP002160132, Unit 11.2 (1988).

*Primary Examiner*—Deborah J. R. Clark
*Assistant Examiner*—Christopher E. Drabik
(74) *Attorney, Agent, or Firm*—Cheryl L. Becker

(57) ABSTRACT

The subject invention relates to a promoter which induces expression of the myostatin gene as well as to methods for identifying compositions useful for the inhibition of the promoter, and also methods and compositions useful for preventing the synthesis, secretion and function of myostatin. In particular, inhibitors that prevent the synthesis, secretion and function of myostatin may be used to prevent the loss of muscle mass in humans and animals.

5 Claims, 7 Drawing Sheets

Human Myostatin Promoter Sequence
(Search for potential binding sites with MatInspector V2.2)

```
   1 TTCTCTACCCACTCACCCTAATGATGCAGTACTGTCCTGTCTCCTTGGTGATAAGAACTGCCAGAACTGGGTCTCCAGCAGTCAGACTCATTGAAGTTT
                                                    GATA                                          NFAT
 101 CCTATAGCTGGTGAGCCCTTCTATTCTGGGGCCTCAGGAAGGTGCAATCACTGCCACTGGAGAAGGAATAAAACTTACTAAATTTCTTCAGTTCTTCT
                                                GFI1
 201 TCACCCATTCAATACTGTTCTCTAGAGAAGTTGATTAGATATAGTCAATTCATTCTCCCTATTCATAGTTATGTTCTATAAAGTCATTGCCAACACTGAGT
 301 TAGCAAATATTGAACTATTGTTCCCAGGGGAAAAACAGGGTTAGTTGAGCCTCTGGTCATAACATTTACATCACCCAATCAATATATAACCTTGTTTAT
 401 GTATGTTTTGTTACAAATACATTATTTAATATATATTGTTCATTCATTAACACTGAACTCACAGCCAGCACTATAACTCAGGCCTGAATGATGCT
 501 TATCTAGCACATGCATTTTTTCATGAGAACTTTTTCCCTTAGGCATATCACAGCCTTTTAAAATTGTGGTAAATATACACAACATTTAGCATCTTAACC
 601 ATTTTTAGGTGTACAGTTCGGTGGCATTAAGCACATTCACACTGTTGTGTAACCATTCATCTTCAGAAATTTTCATCTTCCCAGACTGAA
 701 ACTCTGTATCTATCACACAGTAACTACCCCTCAGTGCCTCACCCAGTCCTGGCAACCACCATGCTACTTTCCATTGCAGCTTTCCTGTGATTAGGAACA
 801 TAGGAACACCACGCAGCACGTCAGCACTATGCTTGGGGGCCATTTTTAAAAGCAAAATCAATAAGAGGAGCAATAAAAGAAGCACAAAATATGTGA
                         CREB
 901 AAACATGGCACTAAATAGACGGGAAAAGGGAATTTGTTTATAGTATGAGAGCTGAAACAAAAGGCGGAACCCTGCCTTGTTGACCTCATCTGGGAAC
                                                                                               IK2
1001 CTGTGCGTCAGATAGGACTCAAATTTTTTGCCGCTCTGTGAATGCCAGCGAATGACTGAAAATGCTAGGAATATTGAGTTTCATAGATAAATTTTAGCA
                                                               AP1
1101 AGTAGGCAAATTTGTGAATACAGAAATCATGAATAATAAGAATTGTCTGTTAGCGGAAATGACAACCTTTGTTCACTTTTTCCAGGTGATAAGAATAAA
                                                                                              GATA
```

FIG. 2A

```
1201  GAGCTGGAACATGTCTTGTAACCTGGCTGCCTTAGAAAATTTACTTGCCTCACAGGCCTAGAAAGTAGGCTTTGTGACTGATAATTGGCAGCTATGACC
                                                                                                    CREB/c-jun
                                                                         AP1
1301  TGAAGCAGTTCTAGTTCATGTGGAGCATAATTTTAAGCATAATCTCAAACCCTTCTGCATAAAACAAAGAGCAAGCACTCAAATGCCAGTTATCAATTAC 1401  TTACTATATGACAGGTGCCATATTCAGCAATTTACATGCATTATTAAATTATATCCCCCAAAACCCTATGAGGAAGCTAAAGTTAGGGAAGTTAAGTA
                        myoD             CEBP 1501  TCTCATCCATTATCACATAGTTAGAAGTGGCAAAGTTGAGATTTGAACTCAGGTCTATCTGACTCCAGAGCCTGAGTTCTCAATTCAACTGTATACAAT 1601  TCTAAGCATATTAAAAAAAAGTTTGACTTACTTGGAACTGTATAGATGCATGTGTTACAATGATCATAACATTGAAAGATTTACACATTGAAAAATGA 1701  ATTTACCAAACAAATAAAACCTTAGAAGCCAGATCTAATATTGTCCCATAACAAAGAGTATCTGAAATCCTCAGGGCATCTGGTTTGTGTCTGGTTTCC 1801  TTAATCTTTAATGATGAGCAAATCCAATGCATTATGTAAGGCCATTTTTTCTCAAGAGATGTAGATACCTCTTAAGAATTTGATGAAAATGCATTAACT
                                              E4BP4

1901  TTTCAGGCTACTGAGTTGCATTTTAGTGCACCGAGGCAGTAAATTAGTGTACAGTGTGCAAAAATGGTAGTGACTTTAAAAATAAATATTTGATATGAGC

2001  CACTGTATTCTCTTGGAAAAAAAAGTAATGGACTAAATCTCTTAGCTTCCCAAAAAGGAGTAGGAAAAAGAAATCTCCTTTGGCCTAGA
              NFAT                                                                        NFAT

2101  AATATCTTCTGTTTCTTGCTGGCTATGTTTGCTTAGCTCTTAATAGTTCATTTGACTAGATCTCTTGTGGCTCCCAAAGCTAAGGTTGAACGTTGATCCC

2201  TACAGAGGCCACTTAAATTTAGAGAACAAAAAGCTCTATTCTCTGCTCCCAGACTTTACCCCCAAATCCCTGCCAGGTGTCTGCCCTCTGGTCAAAATGAG
                                                                                myoD 2301  AAATTGGCAAAGGGGTGCAAAACATCGCAGTATTGGGAAACAACAAAAGGTCACCCCTTTATCATGATGCTCTTTCTCTTTATGTGCTCATAATATTC
                                              IK2

2401  TGATATAATTTATAGAGAATAGATACTGCACTTTTACTCTCTGGATATTTACTGCTGGAAATCTGAGGCAAACTGTAATAATCTCTGCCATGCCAGTTA
                            GATA
```

FIG.2B

```
2501  TAAAATTCATTATCTTAGTCTATGTTCAGAGATTTTCTACTAGTGGCATTACCCTCTTGGTAATAAACAATGAAAAACACATCTTCTGAGTTATGTTA
                 GATA                                              SOX5
2601  ATCTGCATCTTAGAATAGGAAATATAGCACTCAGTCAAAAGTTCAGTATAATTTCATATTAATAAAGACATGAAACTATGTAAAATAATTCCATG
                 NFAT
2701  CACAATATGTTATAATAACAATGACTTCCAATATTACTAAGAATTAGTCAGAAAACAAGTTTCTCAAATTATAGATGAAAATTCTCAACTAGTATCAT
2801  AATCTTAACTTTTAATTCAGGTCTTCCTAATTTTTATTTTCCTAATTACTTGGCACTAAAAATAATTAATACAACAATAAAAATATTTCTACTTCAA
                                        S8
2901  ATACTTGCCTAAACAATATAAAATCATTTAGTTTTTGAGGAAGTAAATATTTCATATTTAAATATGTAGTATAAATTAAAATTGACTTATTTAAATTAC
           SOX5
3001  AATAAGAGTTGTGTGAGGATTAGTAAGATTTAAGTACAGTTTATATTATTGCCAACATAGACTTTTGTTTTCAAATGTCACAAATATCTTTTATTATTT
3101  GTAGATTTATTTCTTTATGAAGTAGTCAAATGAATCAGCTCACCCTTGACTGTAACAAAATACTGCTTGGTGACTTGGGACAGACAGGGTTTTAACCTC
                                         AP1
3201  TGACAGGCGAGATTCATTGTGGAGCAAGAGCCAATCATAGATCCTGACGACACTTGTCTCATCTAAGTTGGAATATAAAAGGCCACTTGGAATACAGTATA
                                       CCAAT Binding Site                              TATA Box
3301  AAAGATTCACTGGTGTGGCAAGTTGTCTCTCAGACTGTACATGCATTAAAATTTTGCTTGGCATTACTCAAAAGCAAAAGAAAAGTAAAAGGAAGAAACA
3401  AGAACAAGAAAAAAGATTATATTGATTTTAAAATCATG
```

FIG. 2C

MYOSTATIN GENE PROMOTER AND INHIBITION OF ACTIVATION THEREOF

BACKGROUND OF THE INVENTION

1. Technical Field

The subject invention relates to a promoter which regulates expression of the myostatin gene as well as methods of inhibiting this promoter and compositions used for such inhibition. In particular, inhibitors of the promoter prevent the expression of the myostatin gene and thus prevent muscle wasting.

2. Background Information

Myostatin, or growth/differentiation factor 8 (GDF-8), belongs to the transforming growth factor-β (TGF-β) superfamily (McPherron et al., *Nature* 387:83–90 (1997)). The human myostatin gene has been cloned (Nestor et al. *Proc. Natl. Acad. Sci.* 95:14938–43 (1998)), and it has been reported that myostatin immunoreactivity is detectable in human skeletal muscle in both type 1 and type 2 fibers. With respect to function, myostatin may play a role in negatively regulating the growth and development of skeletal muscle (Nestor et al., supra).

The first evidence that myostatin may play a key role in negatively regulating muscle development came from a study with myostatin knock-out mice (McPherron et al., *Nature* 387:83–90 (1997)). In the myostatin null mice, the animals were rather normal except that they were significantly larger than wild-type mice and had a large and widespread increase in skeletal muscle mass. Furthermore, it was also determined that two breeds of cattle, characterized by increased muscle mass, have mutations in the myostatin coding sequence (McPherron et al., *Proc. Natl. Acad. Sci.* 94:12457–61 (1997)). Additionally, it should be noted that the serum and intramuscular concentrations of immunoreactive myostatin are increased in HIV-infected men with muscle wasting compared with healthy men, and correlate inversely with the fat-free mass index. These data support the hypothesis that myostatin is a negative regulator of skeletal muscle growth in adult men and contributes to muscle wasting in HIV-infected men (Nestor et al., supra).

In view of the above findings, a need exists for a manner of regulating myostatin expression, particularly in individuals who experience muscle wasting as a result of a condition or disease state such as, for example, aging, Autoimmune Deficiency Syndrome (AIDS), Multiple Sclerosis, and cancer. The present invention provides methods and compositions which may be utilized to help individuals with such muscle wasting conditions and provides further insight into the regulation of myostatin gene expression.

All U.S. patents and publications referred to herein are hereby incorporated in their entirety by reference.

SUMMARY OF THE INVENTION

The present invention encompasses an isolated nucleic acid sequence represented by FIG. 2 (SEQ ID NO:1).

Additionally, the present invention encompasses a vector comprising the above-described nucleic acid sequence and a nucleic acid sequence encoding a reporter molecule. The nucleic acid sequence encoding the reporter molecule is operably linked to the nucleic acid sequence represented by FIG. 2. The reporter molecule may be selected from the group consisting of, for example, luciferase, β-galactosidase and Chloramphenicol Acetyltransferase (CAT). Preferably, the reporter molecule is luciferase. The present invention also includes a host cell comprising the above-described vector.

Additionally, the present invention includes a purified antibody produced in response to immunization with myostatin as well as a composition comprising this purified antibody.

Furthermore, the present invention also includes a method of identifying a composition which inhibits activation of the myostatin promoter. This method comprises the steps of: a) constructing a vector comprising a nucleic acid sequence represented by FIG. 2 (SEQ ID NO:1) and a nucleic acid sequence encoding a reporter molecule, the nucleic acid sequence encoding the reporter molecule being operably linked to the nucleic acid sequence encoding the sequence represented by FIG. 2; b) introducing the vector into a host cell for a time and under conditions suitable for expression of myostatin; c) exposing the host cell to a composition which may inhibit activation of the myostatin promoter and a substrate specific for the reporter molecule; and d) measuring the signal generated by reaction of the reporter molecule and the substrate in comparison to that produced by a control host cell, a smaller signal by the host cell of (c) indicating that the composition will inhibit activation of the myostatin promoter.]

Also, the present invention includes a method of identifying a composition which inhibits expression of myostatin comprising the steps of: a) adding an antibody selected from the group consisting of a monoclonal or a polyclonal antibody produced against myostatin to a solid phase; b) adding known concentrations of myostatin or a cell sample comprising myostatin exposed to the test composition, to the solid phase, in order to form a first complex between the antibody and the known concentrations of myostatin or myostatin in said cell sample; c) adding a second antibody to the first complex, selected from the group consisting of a monoclonal antibody or a polyclonal antibody produced against myostatin for a time and under conditions sufficient for formation of a second complex between the first complex and the second antibody; d) contacting the second complex with an indicator reagent which comprises a signal generating compound attached to an antibody against said antibody of said second complex, for a time and under conditions sufficient for formation of a third complex; e) detecting the presence of a measurable signal, absence of the signal indicating that the composition inhibits expression of myostatin and presence of the signal indicating that the composition does not inhibit expression of myostatin.

Moreover, the present invention also includes a method of identifying a composition which inhibits expression of myostatin comprising the steps of: a) coating a fixed amount of myostatin on a solid phase; b) adding known concentrations of myostatin or a cell sample comprising myostatin exposed to the composition; c) contacting an antibody selected from the group consisting of a monoclonal antibody or a polyclonal antibody produced against myostatin to the myostatin in (a) and (b) for a time and under conditions sufficient to form a first complex, wherein myostatin of (a) competes with the myostatin of (b), in a competition for the antibody; d) contacting the complex with an indicator reagent which comprises a signal generating compound attached to an antibody against the antibody of the first complex, for a time and under conditions sufficient to form a second complex; and e) detecting a measurable signal, a higher signal as compared to a control, indicating the composition inhibits myostatin expression.

Additionally, the present invention includes a method of identifying a composition, in a mixture of compositions, which prevents myostatin from binding to a myostatin receptor comprising the steps of: a) mixing purified myostatin with the mixture of compositions; b) passing the resulting mixture of step (a) through a filter having pores of a size such that a composition which is complexed to myostatin does not pass through the filter; and c) determining the structure of a complexed composition, thereby identifying a composition which prevents myostatin from binding to a myostatin receptor.

Also, the present invention encompasses a method of identifying a composition which prevents myostatin from binding to a myostatin receptor comprising the steps of: a) radiolabeling recombinant myostatin; b) incubating the radiolabeled myostatin with cells or membranes comprising a myostatin receptor; c) contacting the incubated mixture of step (b) with a composition of interest; d) separating radiolabeled myostatin bound to cells or membranes from unbound myostatin; and e) determining the amount of radioactivity in bound myostatin, compared to a control, a lower level of radioactivity in bound myostatin compared to said control indicating a composition which inhibits myostatin from binding to a receptor.

Furthermore, the present invention includes a method of preventing muscle wasting in a mammal comprising administering to the mammal a composition comprising an active ingredient which causes an effect selected from the group consisting of preventing activation of the myostatin promoter, preventing synthesis of myostatin, and preventing myostatin from binding to its target receptor, in a therapeutically effective amount, such that muscle wasting is prevented.

BRIEF DESCRIPTION OF THE DRAWINGS

FIG. 2 represents the nucleic acid sequence of the human myostatin promoter region. The putative transcription factor binding regions are identified and underlined.

DETAILED DESCRIPTION OF THE INVENTION

Figure 1:
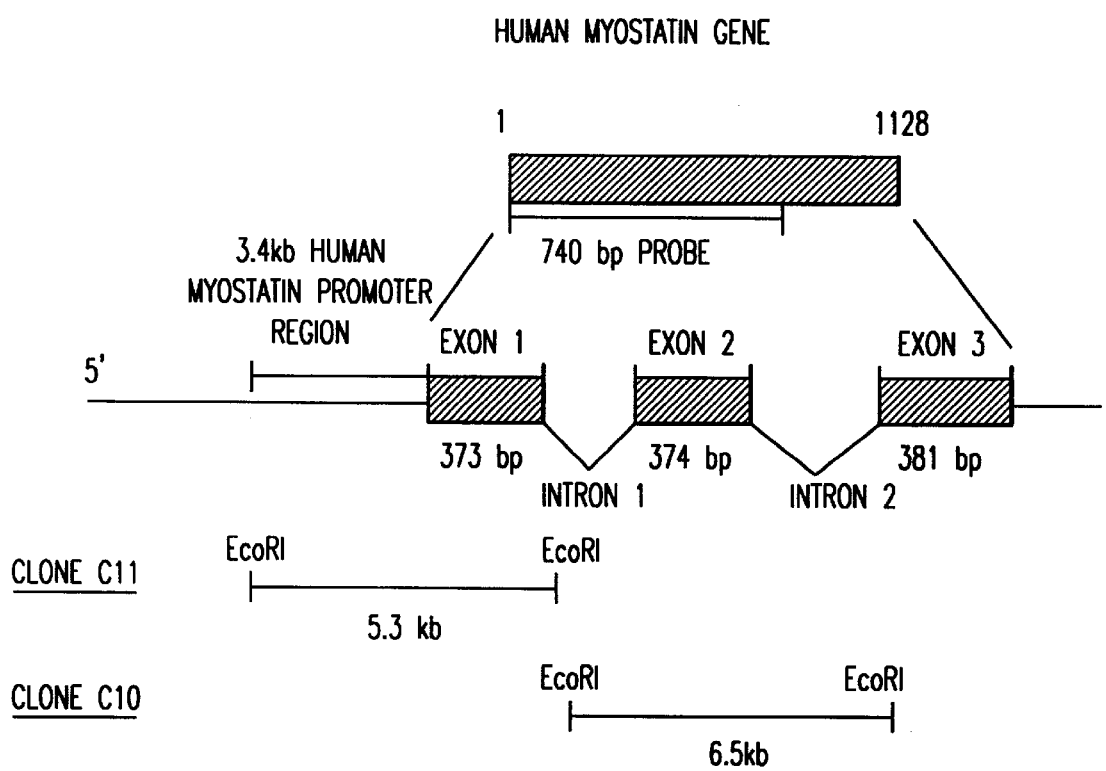
FIG. 1 represents a conceptual illustration of the human myostatin gene. The human myostatin gene contains three exons and two introns, which encode 1.1 kb of myostatin cDNA. When a human P1-derived Artificial Chromosome (PAC) library was screened using a 740 bp probe encoding human myostatin exon 1 and 2, one positive clone with a 120 kb insert was identified. After digesting the clone with EcoRI, two human genomic subclones were isolated. One of the subclones, Clone C11, contained 0.37 kb of exon 1, 1.53 kb of intron 1, and a 3.4 kb sequence containing the human myostatin promoter region.

As noted above, the subject invention relates to the identification and isolation of a promoter which is involved in activating or regulating expression of the myostatin gene. Myostatin negatively regulates the growth and development of skeletal muscle.

In particular, the subject invention relates to methods which may be used to identify compounds that inhibit the myostatin promoter activities. The myostatin promoter region or nucleic acid sequence which regulates the expression of myostatin is linked to the luciferase reporter gene. Thus, if one is able to identify compounds that inhibit the activity of the myostatin promoter region to prevent expression of luciferase, one may then prevent the promoter region from functioning, thereby preventing expression of myostatin.

The identification of compounds which inhibit the myostatin promoter activity and luciferase production may be carried out by the use of drug screening assays. Initially, a vector is created comprising an isolated DNA sequence encoding the promoter region of myostatin, which is linked to the luciferase reporter gene. The vector may be, for example, a plasmid, a bacteriophage or a cosmid. The vector is then introduced into host cells under time and conditions suitable for activation of the myostatin promoter. The host cells may be prokaryotic or eukaryotic cells. Preferably, eukaryotic cells are utilized, for example, cell lines with muscle lineage. Examples include human skeletal muscle cells, human rhabdomyosarcoma cells, and rat L6 or L8 cells. The host cells are then exposed to the test composition thought to block activation of the myostatin promoter and luciferase gene expression. The cells are also exposed to a substrate for luciferase. One then measures the quantity of signals or light emitted from the luciferase-substrate reaction. If the amount of signals produced by the host cells, exposed to the composition in question, is lower than that produced by control cells (i.e., cells which have not been exposed to the composition), then the composition has inhibited the activity of the myostatin promoter, and will be useful in inhibiting the expression of the myostatin gene. If the amount of signals produced by the treated cells is equal to that produced by the control cells, the composition has not inhibited the activity of the myostatin promoter and will not prevent myostatin gene expression.

Once compositions have been identified which inhibit the activity of the myostatin promoter, such compositions may be administered to patients having any type of condition involving muscle wasting, for example, Acquired Immunodeficiency Syndrome (AIDS), cancer, Multiple Sclerosis and aging. The pharmaceutical composition may comprise a therapeutically effective amount of the inhibitor and an appropriate physiologically acceptable carrier (e.g., water, buffered water or saline). The dosage, form (e.g., suspension, tablet, capsule, etc.), and route of administration of the pharmaceutical composition (e.g., oral, topical, intravenous, subcutaneous, etc.) may be readily determined by a medical practitioner and may depend upon such factors as, for example, the patient's age, weight, immune status, and overall health.

Additionally, the present invention also encompasses compositions comprising antibodies derived using purified myostatin protein or a portion thereof which may be administered with, for example, an appropriate carrier (e.g., water, buffered water or saline). Subsequent to administration of the antibodies, they may bind to expressed myostatin in the body in order to form a complex, thereby preventing the expressed myostatin from negatively regulating muscle development. The antibodies themselves, as well as portions thereof, are also encompassed within the scope of the present invention, as well as assays which comprise such antibodies or portions thereof.

It should be noted that the above pharmaceutical compositions and antibodies may be utilized for veterinary applications (e.g., for preventing muscle wasting in aging or diseased animals) or for agricultural applications (e.g., for increasing the meat production in livestock, since animals without myostatin exhibit a much larger muscle mass). For example, the therapeutic composition which inhibits the activity of the myostatin promoter may be administered to mammals such as, for example, horses, cows, sheep, goats, cats, dogs and pigs.

The present invention also covers two methods, using purified myostatin and/or myostatin antibodies, which identify compositions that inhibit the synthesis and the secretion of the myostatin protein. In the sandwich method, a mammalian monoclonal and/or polyclonal antibody (e.g., rabbit or mouse) against the mature form of myostatin is coated on a solid surface (e.g., the Immulon-4 plate (Dynatech Laboratories INC., Chantilly, Va.)). The surface will be blotted by a known blotting agent, for example, Bovine Serum Albumin (BSA), and washed. Samples (e.g. supernatants from human skeletal muscle cells treated with or without test agents) or known concentrations of purified mature form of myostatin are added to the surface (e.g., plate). After myostatin binds to the antibody or antibodies, the surface will be washed, and then incubated with a mammalian monoclonal and/or polyclonal antibody (e.g., goat, rabbit or mouse) against myostatin. The binding of the second anti-myostatin antibody will be detected by use of an indicator reagent which comprises an antibody conjugated with a signal generating compound, for example, an enzyme. A substrate for the enzyme is also added if an enzyme is utilized. For example, horseradish peroxidase (HRP) and its substrate O-Phenylenediamine hydrochloride (OPD) may be utilized. In particular, the enzyme-substrate reaction generates a detectable signal or change, for example, color, which may be read, for example, in a Microplate Reader. Examples of signal generating compounds, other than an enzyme which may be utilized include, for example, a luminescent compound, a radioactive element, a visual label and a chemiluminescent compound. Known concentrations of purified myostatin are used to generate a standard curve. The concentration of myostatin in the unknown samples (e.g. supernatants from human skeletal muscle cells treated with or without test agents) can be determined using the standard curve. The test agents which decrease the myostatin concentration in supernatants are potentially useful for inhibition of myostatin synthesis/secretion.

In the competitive method, a fixed amount of human myostatin is coated on a solid surface, for example, the Immulon-4 plate. The plate will be blotted by, for example, BSA or another known blotting agent, and washed. Samples (e.g., supernatants from human skeletal muscle cells treated with or without test agents) or known concentrations of purified mature form of myostatin are added to the plate along with a mammalian monoclonal and/or polyclonal antibody (e.g., goat, rabbit or mouse) against myostatin. The plate will be washed, and then incubated with an indicator reagent comprising an antibody conjugated with a signal generating compound, for example, an enzyme (or the entities described above). If an enzyme is used, a substrate for the enzyme is also provided. The enzyme may be, for example, horseradish peroxidase (HRP) The substrate may therefore be O-Phenylenediamine hydrochloride (OPD)). Again, the enzyme-substrate reaction generates a detectable change or signal, for example, color, which can be read in, for example, a Microplate Reader. Known concentrations of purified myostatin may be used to generate a standard curve. The concentration of myostatin in the unknown samples (e.g. supernatants from human skeletal muscle cells treated with or without test agents) can be determined using the standard curve. The test agents which decrease the myostatin concentration in supernatants are potentially useful for inhibition of myostatin synthesis/secretion. Known concentrations of myostatin, or myostatin in the sample, compete with myostatin protein coated on the plate in binding to myostatin antibodies. When more myostatin is present in the sample, less signal is generated. If a test agent is able to block myostatin synthesis/secretion, the amount of myostatin in that particular sample will be less than in the control, and the signal in that sample will be more than in the control.

Additionally, the present invention covers an Affinity-Selection method, using purified myostatin in a filtration assay, to identify compositions that bind to myostatin to prevent myostatin from binding to its receptors, thus preventing myostatin from functioning. Briefly, purified myostatin is mixed with several test compounds. The mixture is passed through a filter which only allows certain molecular weight molecules to pass through. Compositions that bind to myostatin will be retained by the filter. The unbound compounds are not retained and can be separated from the bound compositions. The structures of the compositions which bind to myostatin are determined, for example, by Mass Spectrometry.

Furthermore, the present invention also encompasses a receptor binding method using radiolabeled myostatin to bind to cells or membranes prepared from tissues or cells containing myostatin receptors. In this manner, one may identify compositions that block myostatin from binding to its receptors, thus preventing myostatin from functioning. In particular, the purified recombinant myostatin protein from bacteria, insect or mammalian cells is radiolabeled ([$^{125}$I], [$^{3}$H], [$^{14}$C], etc.). The radiolabeled myostatin is then incubated with cells or membranes prepared from tissues or cells which contain myostatin receptors in the presence or absence of the test composition. Radiolabeled cells and membranes are then separated from non-radiolabeled cells and membranes by separation methods such as, for example, filtration and centrifugation. The amount of myostatin binding to cells or membranes is determined by counting radioactivity. A decrease in radioactivity in the presence of a test composition indicates that the composition inhibits myostatin binding, and thus is useful in inhibiting myostatin function.

The present invention may be illustrated by the use of the following non-limiting examples:

EXAMPLE I

Identification of the Nucleotide Sequence Encoding the Human Myostatin Promoter and Potential Transcription Factors Binding Regions 1. Cloning of Human Myostatin cDNA Human myostatin cDNA was amplified from human skeletal muscle 5'-plus cDNA library (Clontech, Palo Alto, Calif.) by PCR using specific primers, 5'-ATG CAA AAA CTG CAA CTC TGT GTT T-3' (SEQ ID NO: 2) and 5'-TCA TGA GCA CCC ACA GCG GTC-3' (SEQ ID NO: 3). PCR products were cloned into eukaryotic TA cloning vector pCR3.1 (Invitrogen, Carlsbad, Calif.). Insertion was confirmed by DNA sequencing.

2. Cloning of the Human Myostatin Promoter Region

The EcoRI and HindIII fragment (740 bp) of human myostatin cDNA (FIG. 1), which covers exon 1 and 2 of human myostatin gene, was sent to GenomeSystems Inc.

(St. Louis, Mo.) as a probe to screen the human P1-derived Artificial Chromosome (PAC) library. One positive clone with 120 kb insert was identified and confirmed by genomic Southern blot using the same probe. The 120 kb insert was digested with EcoRI restriction enzyme, and subcloned into plasmid pZero (Invitrogen, Carlbad, Calif.). Two positive subclones with 5–7 kb insert were identified (FIG. 1). Sequencing results indicate that clone 10 contains exon 2 and part of intron 1 and 2. Clone 11 (5.3 kb) contains exon 1, part of intron 1, and a 3.4 kb 5' untranslated region—the putative myostatin promoter region. Program MatInspector V2.2 (Gesellschaft fur Biotechnologische Forschung mbH, Braunschweig, Germany) was searched to identify potential transcription factor binding regions (FIG. 2). MatInspector is a software that allows fast scanning of sequence data for consensus motifs. MatInspector uses the core similarity, the matrix similarity and the Ci vector created by MatInd to calculate similarity index. The potential transcription factor binding sites were selected when both core similarity and matrix similarity reach 0.95. The details of the program are illustrated in Quandt et al., *Nucleic Acids Research* 23:4878–4884, 1995.

Figure 3:
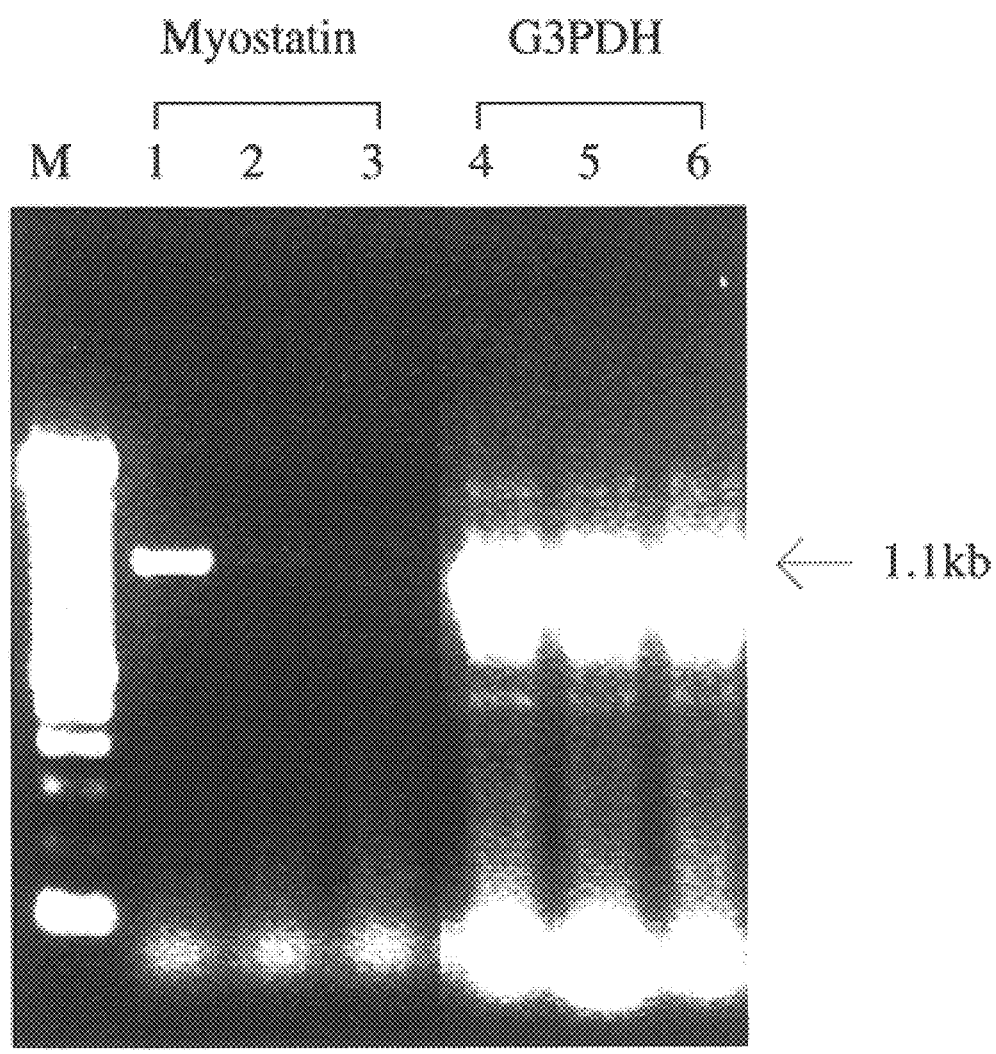
FIG. 3 represents the detection of myostatin mRNA by RT-PCR of RNA samples from human skeletal muscle, rhabdomyosarcoma cells, and prostate smooth muscle cells using human myostatin-specific primers, and for G3PDH using G3PDH-specific primers. Amplified myostatin gene (1.1 kb) was observed in both human skeletal muscle cells (lane 1) and rhabdomyosarcoma cells (lane 2), but not in prostate smooth muscle cells (lane 3). Amplified G3PDH gene (0.9 kb) was observed in skeletal muscle (lane 4), rhabdomyosarcoma cells (lane 5), and prostate smooth muscle cells (lane 6).

3.Identification of Human Skeletal Muscle Cells or Other Cell Lines of Muscle Lineage which Express Myostatin Total RNA from human skeletal muscle cells and rhabdomyosarcoma cells was isolated using Trizol reagent (Life Technologies, Gaithersburg, Md.) and used as templates for reverse transcription. The myostatin gene was amplified by PCR using human myostatin specific primers, 5'-ATG CAA AAA CTG CAA CTC TGT GTT T-3' (SEQ ID NO: 2) and 5'-TCA TGA GCA CCC ACA GCG GTC-3' (SEQ ID NO: 3). Total RNA from human prostate smooth muscle cells were also tested. Primers for endogenous G3PDH gene was used to test the integrity of total RNA. The PCR products were analyzed on a 1% agarose gel (FIG. 3). The 1.1 kb PCR products, 1.1 kb being the correct size for myostatin, indicated that both human skeletal muscle cells and rhabdomyosarcoma cells express myostatin.

EXAMPLE II

Luciferase Assay

The luciferase reporter gene assay was designed for quantitative analysis of mammalian gene expression. The coding region for firefly (Photinus pyralis) luciferase was linked to the 3.4 kb 5' untranslated region (5-UTR) of the human myostatin gene. The construct was transiently transfected into human skeletal muscle cells or human rhabdomyosarcoma cells, and after 48 hours, luciferase activity was measured. To assay for the luciferase activity, luciferin and $Mg^{2+}$-ATP were added to cellular extracts, and the production of light was monitored. The luciferase activity is increased if the 3.4 kb 5'-UTR region has promoter activity. Therefore, the luciferase activity may be used as an indicator (reporter) of the function of the upstream promoter region.

Figure 4:
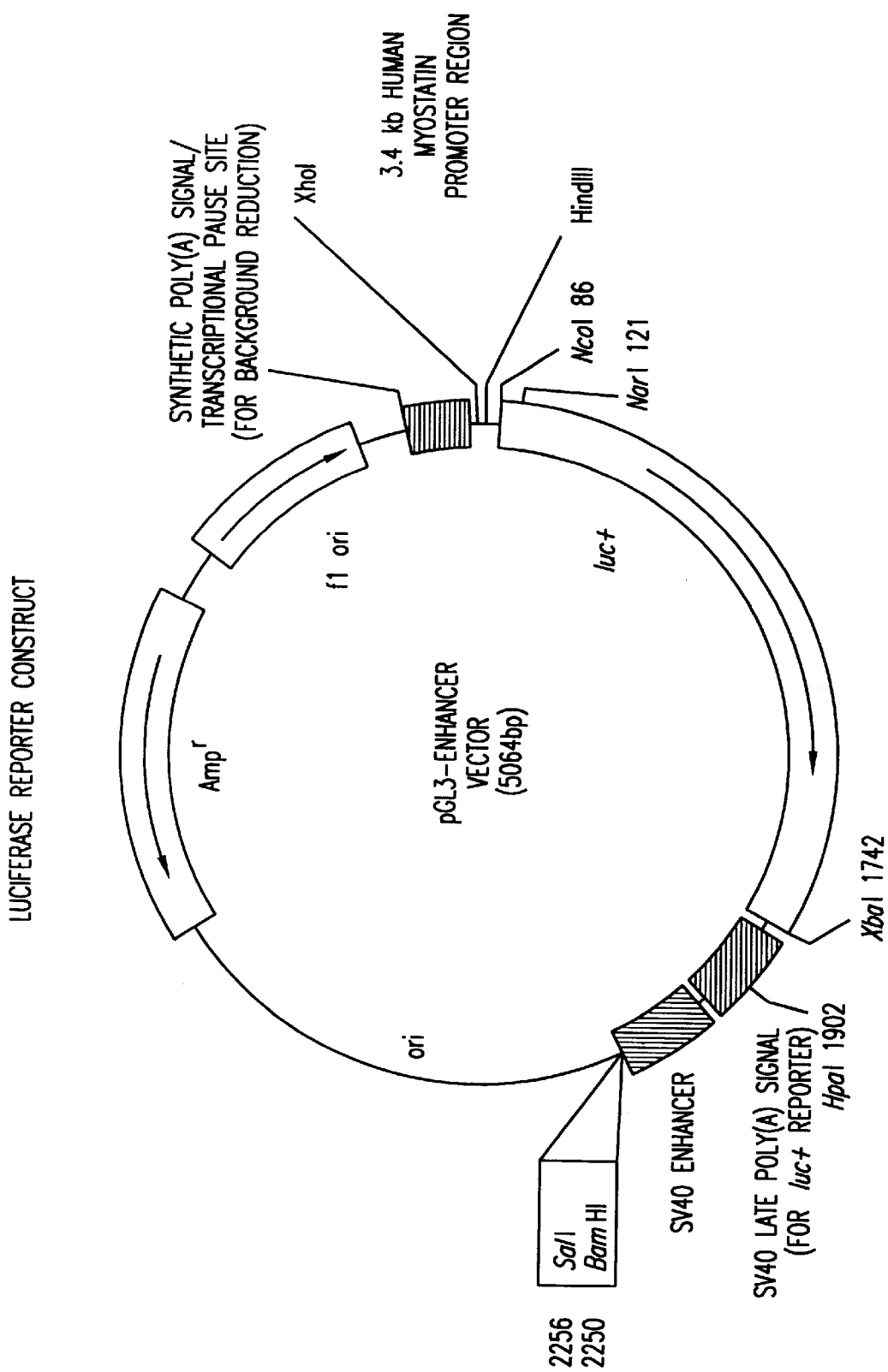
FIG. 4 represents the luciferase reporter constructs. The 3.4 kb human myostatin promoter region was cloned into the XhoI and HindIII sites of a luciferase reporter pGL3-enhancer vector (Promega, Madison, Wis.), which contained a luciferase reporter gene and a SV40 enhancer element for increasing the transcription level.
Figure 5A:
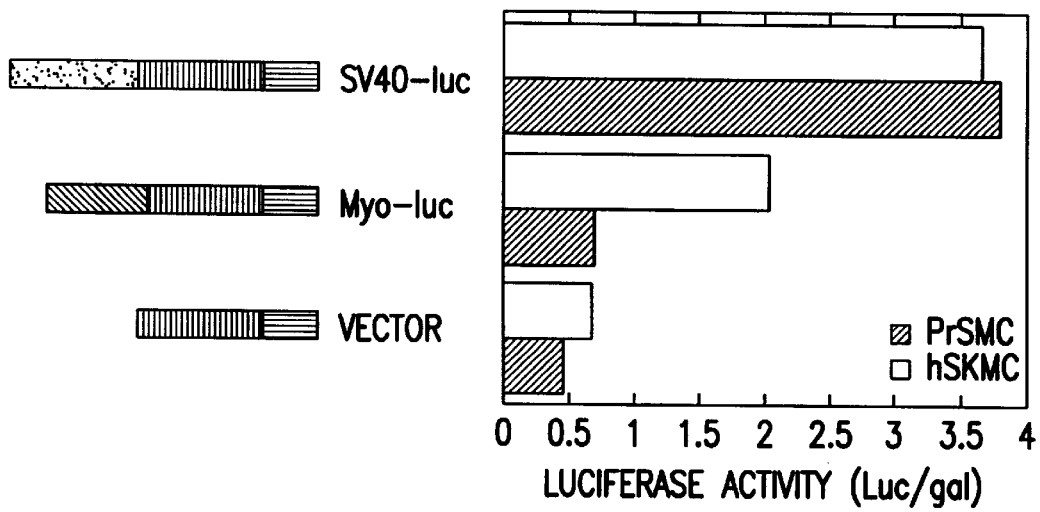
FIG. 5 represents results from a luciferase assay for the human myostatin promoter region in human skeletal muscle cells and rhabdomyosarcoma cells.
Figure 5B:
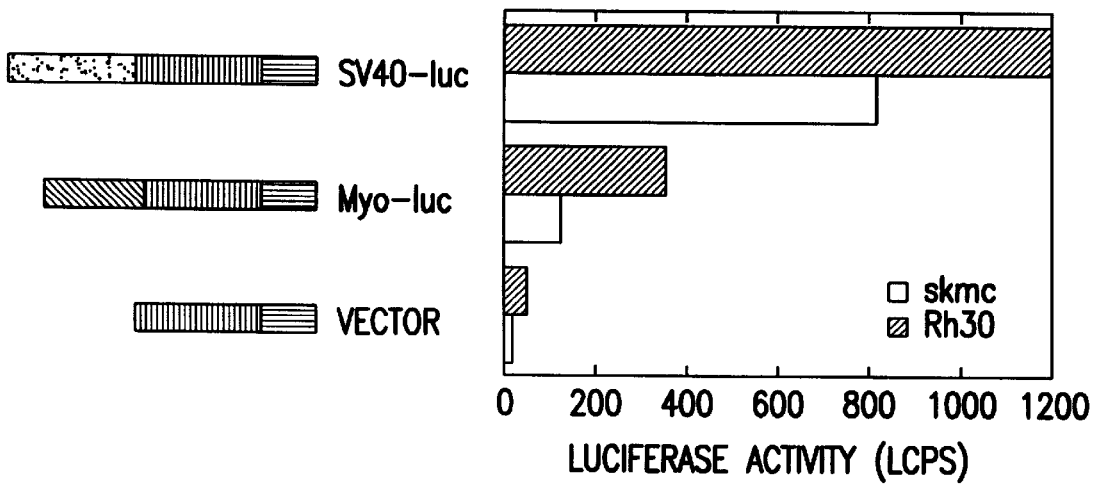

The 3.4 kb human myostatin 5' untranslated region was cloned into XhoI and HindIII sites of pGL3-enhancer vector (Promega, Madison, Wis.), linked to the luciferase reporter gene (FIG. 4). The construct was transiently transfected into human skeletal muscle cells or human rhabdomyosarcoma cells using Superfect reagents (Qiagen, Inc., Santa Clarita, Calif.). Another reporter gene such as β-galactosidase gene or Renilla luciferase gene was co-transfected as control for transfection efficiency. Cells were lysed in lysis buffer after 48 hours, and cellular extracts were assayed for luciferase and β-gal activity using detection kit [e.g. LucLite (Packard, Meriden, Conn.), luminescent β-galactosidase detection Kit II (Clontech, Palo Alto, Calif.), or dual-luciferase reporter assay systems (Promega, Madison, Wis.)]. The pGL3-enhancer parental vector was used as a negative control and the pGL3-control vector with SV40 promoter was used as a positive control for the luciferase activity. The luciferase activity was counted on a luminescent light detector such as a MicroBeta counter or a Luminometer (EG & G Life Sciences-Wallac, Turku, Finland), and the result was normalized by transfection efficiency. There was about a 5-fold increase of luciferase activity for the human myostatin promoter construct in comparison to its parental vector in human skeletal muscle cells (FIG. 5A). In human rhabdomyosarcoma cells, the increase of luciferase activity was about 7-fold (FIG. 5B). As expected, the luciferase activity was not increased in human prostate smooth muscle cells (FIG. 5A), which do not express myostatin.

In view of the above results, the luciferase reporter construct containing the 3.4 kb human myostatin promoter region may be stably or transiently transfected into mammalian cell lines such as SV-40-transformed human skeletal muscle cells or rhabdomyosarcoma cells and others for high through-put screening. Luciferase activity may be used as an indicator for selecting compounds which inhibit expression of the myostatin gene.

EXAMPLE III

Enzyme-Linked Immunosorbent Assay (ELISA) for High Throughout Screening

Sandwich or competitive ELISA may be used to identify compounds which inhibit human myostatin protein synthesis and/or secretion. In the sandwich ELISA, for example, a rabbit or mouse monoclonal and/or polyclonal antibody against the mature form of myostatin is coated on the Immulon-4 plate (Dynatech Laboratories, Inc., Chantilly, Va.), and the plate is blotted by BSA, and washed. Samples (e.g., supernatants from human skeletal muscle cells treated with or without test agents) or known concentrations of purified mature form of myostatin are added to the plate. After myostatin protein binds, the plate is again washed, and then incubated with a goat or rabbit or mouse monoclonal and/or polyclonal antibody against myostatin. The binding of the second anti-myostatin antibody will be detected by an antibody conjugated with horseradish peroxidase (HRP) using O-Phenylenediamine hydrochloride (OPD) as the substrate. Known concentrations of myostatin are used for generating the standard curve.

In the competitive ELISA, human myostatin protein is coated on the Immulon-4 plate, and the plate is blotted by BSA, and washed. Samples (e.g., supernatants from human skeletal muscle cells treated with or without test agents) or known concentrations of purified mature form of myostatin or myostatin peptides are added to the plate along with a goat or rabbit or mouse monoclonal and/or polyclonal antibody against myostatin. The plate is again washed, and then incubated with an antibody conjugated with horseradish peroxidase (HRP) using O-Phenylenediamine hydrochloride (OPD) as the substrate. The known concentrations of myostatin are used for generating the standard curve.

Human skeletal muscle cells or other cell lines of muscle lineage which synthesize and secrete myostatin may be used to test compounds thought to inhibit the synthesis or secretion of myostatin. Cells are incubated with test compounds for a period of time, e.g., 6–48 hours. The amount of myostatin in the medium of cells is then determined by ELISA. A decrease in the amount of myostatin indicates that the test compound is effective in inhibiting the synthesis and secretion of myostatin, whereas an increase in the amount of myostatin or maintenance of the same level of myostatin indicates that the test compound is not effective in inhibiting the synthesis and secretion of myostatin.

EXAMPLE IV

Production of Radiolabeled Myostatin for Use in Receptors Binding Assay

The purified recombinant myostatin protein from bacteria, insect or mammalian cells is radiolabeled ($[^{125}I]$, $[^{3}H]$, $[^{14}C]$, etc.). The radiolabeled myostatin is then incubated with cells or membranes prepared from tissues or cells which contain myostatin receptors in the presence or absence of the test composition. The amount of myostatin binding to membranes is determined by counting radioactivity. A decrease in radioactivity in the presence of a test composition indicates that the composition inhibits myostatin binding, and thus is useful in inhibiting myostatin function.

EXAMPLE V

Purified Myostatin Used in Affinity Selection

The purified recombinant myostatin protein from bacteria, insect or mammalian cells is used in binding test compositions. In particular, test compositions that bind to myostatin are retained by filter, and the structure is determined by Mass Spectophotometry. A test composition that binds to myostatin is useful in inhibiting the binding of myostatin to its receptor, thus inhibiting myostatin function.

What is claimed is:

1. An isolated nucleic acid sequence comprising SEQ ID NO:1.

2. A vector comprising said nucleic acid sequence of claim 1 and a nucleic acid sequence encoding a reporter molecule, said nucleic acid sequence encoding said reporter molecule being operably linked to said nucleic acid sequence of claim 1.

3. The vector of claim 2, wherein said reporter molecule is selected from the group consisting of luciferase, β-galactosidase and Chloramphenicol Acetyltransferase (CAT).

4. The vector of claim 3 wherein said reporter molecule is luciferase.

5. An isolated host cell comprising said vector of claim 3.

* * * * *

SEQUENCE LISTING

<160> NUMBER OF SEQ ID NOS: 3

<210> SEQ ID NO 1
<211> LENGTH: 3435
<212> TYPE: DNA
<213> ORGANISM: Homo sapiens

<400> SEQUENCE: 1

```
ttctctaccc actcaccta atgatgcagt actgtcctgt ctccttggtg ataagaactg      60
ccagaactgg gtctccagca gtcagactac attgaagttt cctatagctg gtgagccctt     120
ctattctggg gcctcaggaa ggttgcaatc actgccactg gagaaggaat aaaacttact     180
taaatttctt cagttcttct tcacccattc aatactgttc tctagagaag ttgattagat     240
atagtcaatt ctccctattc atagtagtta tgttctataa agtcattgcc aacactgagt     300
tagcaaatat tgaactattg ttcccagggg aaaaacaggg ttagttgagc ctctggtcat     360
aacatttaca tcacccaatc aatatataac cttgttttat gtatgttttt gtttacaaat     420
acattattta atatatattg ttcattcatt aacactgaac tcacagccag cagcactata     480
actcaggcct gaatgatgct tatctagcac atgcattttt tcatgagaac ttttttccct     540
taggcatatc acagcctttt aaaattgtgg taaatataca caacatttag catcttaacc     600
atttttaggt gtacagttcg gtggcattaa gcacattcac actgttgtgt aaccatcacc     660
accattcatc ttcagaaatt tttcatcttc ccagactgaa actctgtatc tatcacacag     720
taactacccc tcagtgcctc acccagtccc tggcaaccac catgctactt tccattgcag     780
ctttcctgtg attaggaaca taggaacacc acgcagcacg tcagcactat gcttgggggc     840 cattttaaa aagcaaaatc aataagagga gcaataaaaa aagaagcaca aatatgtga      900 aaacatggca ctaaatagac gggaaaaagg gaatttgttt atagtatgag agctgaaaca     960
aaaaggcgga accctgcctt gtttgacctc atctgggaac ctgtgcgtca gataggactc    1020
aaattttttg ccgctctgtg aatgccagcg aatgactgaa aaatgctagg aatattgagt    1080
ttcatagata aattttagca agtaggcaaa tttgtgaata cagaaatcat gaataataag    1140
aattgtctgt tagcggaaat gacaaccttt gttcacttt ttccaggtga taagaataaa     1200
gagctggaac atgtcttgta acctggctgc cttagaaaat tttacttgcc tcacaggcct    1260
agaaagtagg ctttgtgact gataattggc agctatgacc tgaagcagtt ctagttcatg    1320
tggagcataa ttttaagcat aatctcaaac ccttctgcat aaaacaaaga gcaagcactc    1380
```

-continued

```
aaatgccagt tatcaattac ttactatatg acaggtgcca tattcagcaa tttacatgca   1440
ttattaaatt atatccccc  aaacccctat gaggaagcta agtttagggg aagttaagta    1500
tctcatccat tatcacatag ttagaagtgg caaagttgag atttgaactc aggtctatct   1560
gactccagag cctgagttct caattcaact gctatacaat tctaagcata ttaaaaaaaa   1620
agtttgactt acttggaact gtatagatgc atgtgttaca atgatcataa catttgaaag   1680
atttacacat tgaaaaatga atttaccaaa caaataaaac cttagaagcc agatctaata   1740
ttgtcccata acaaagagta tctgaaatcc tcagggcatc tggtttgtgt ctggttttcc   1800 ttaatctttta atgatgagca aatccaatgc attatgtaag gccattttt  tctcaagaga   1860 tgtagatacc tcttaagaat ttgatgaaaa tgcattaact tttcaggcta ctgagttgca   1920
ttttagtgca ccgaggcagt aaattagtgt acagtgtgca aaaatggtag tgactttaaa   1980
aataaatatt tgatatgagc cactgtattc tcttggaaaa aaaagtaat  ggactaaatc   2040 tcttaggaat ccttagcttc ccaaaaagga gtaggaaaaa gaaatctcct ttggcctaga   2100
aatatcttct gtttcttgct ggctatgttt gcttagctct ttaatagttc atttgactag   2160
atcttgtggc tcccaaagct aaggttgaac gtttgatccc tacagaggcc acttaaattt   2220
agagaacaaa aagctctatt ctctgctccc agactttacc ccaaatccct gccaggtgtc   2280
tgccctctgg tcaaaatgag aaattggcaa aggggtgcaa acatatcgca gtattgggaa   2340
acaacaaaag gtcaccccctt tatcatgatg ctctttctct tttatgtgct cataatattc   2400
tgatataatt tatagagaat agatactgca ctttttactc tctggatatt tactgctgga   2460
aatctgaggc aaactgtaat aatctctgcc atgccagtta taaaattcat tatcttagtc   2520
tatgttcaga gattttttcta ctagctggca ttaccctctt ggtaataaac aatgaaaaac   2580
acatcttctg agttatgtta atctgcatct ttagaatagg aaataatagc actcagtcaa   2640
aagttcagta taattttcat attaataaaa gacatgaaac tatgtaaaaa taattccatg   2700
cacaatatgt tataataaca atgacttcca atatttacta agaatttagt cagaaaacaa   2760
gtttctcaaa ttatagatga aaattctcaa ctagtatcat aatcttaact tttaattcag   2820
gtcttcctaa tttttattt  cctaattact tggcactaaa aataatttaa tacaacaaat   2880
aaaaatattt tctacttcaa atacttgcct aaacaatata aaatcatttt agttttgag   2940 gaagtaatat ttcatatttt aaatatgtag tataaattaa aattgactta tttaaattac   3000
aataagagtt gtgtgaggat tagtaagatt taagtacagt ttatattatt gccaacatag   3060
acttttgttt ttcaaatgtc acaaatatct tttattattt gtagatttat ttcttttatg   3120
aagtagtcaa atgaatcagc tcacccttga ctgtaacaaa atactgcttg gtgacttggg   3180
acagacaggg ttttaacctc tgacagcgag attcattgtg gagcaagagc caatcataga   3240
tcctgacgac acttgtctca tctaagttgg aatataaaaa gccacttgga atacagtata   3300
aaagattcac tggtgtggca agttgtctct cagactgtac atgcattaaa attttgcttg   3360
gcattactca aaagcaaaag aaaagtaaaa ggaagaaaca agaacaagaa aaaagattat   3420
attgatttta aaatc                                                   3435
```

<210> SEQ ID NO 2
<211> LENGTH: 25
<212> TYPE: DNA
<213> ORGANISM: Homo sapiens

<400> SEQUENCE: 2

-continued

```
atgcaaaaac tgcaactctg tgttt                                          25

<210> SEQ ID NO 3
<211> LENGTH: 21
<212> TYPE: DNA
<213> ORGANISM: Homo sapiens

<400> SEQUENCE: 3
tcatgagcac ccacagcggt c                                              21
```